United States Patent [19]

Randin

[11] Patent Number: 5,110,291
[45] Date of Patent: May 5, 1992

[54] APPARATUS FOR BENDING DENTAL ROOT CANAL INSTRUMENTS

[75] Inventor: Jean-Claude Randin, Ballaigues, Switzerland

[73] Assignee: Les fils d'Auguste Maillefer, Societe anonyme a Ballaigues, Switzerland

[21] Appl. No.: 712,914

[22] Filed: Jun. 7, 1991

[30] Foreign Application Priority Data

Jun. 8, 1990 [CH] Switzerland .......................... 1931/90

[51] Int. Cl.$^5$ .............................................. A61C 3/00
[52] U.S. Cl. .................................... 433/156; 433/102; 140/106
[58] Field of Search ................. 433/102, 156, 157, 159, 433/162; 140/106

[56] References Cited

U.S. PATENT DOCUMENTS

| 644,932 | 3/1900 | Miller | 433/159 |
|---|---|---|---|
| 3,199,549 | 8/1965 | Wallshein | 140/106 |
| 4,470,289 | 9/1984 | Sinclair et al. | 140/106 |
| 4,708,651 | 11/1987 | Buchanan | 433/102 |
| 4,889,487 | 12/1989 | Lovaas | 433/102 |

Primary Examiner—John J. Wilson
Attorney, Agent, or Firm—Silverman, Cass & Singer, Ltd.

[57] ABSTRACT

Apparatus for bending dental instrument for use in root canals. The apparatus includes two rotatable sleeves made of plastic material one of which is carried by a stationary element which acts as a handle and the other one of which is carried by a movable member articulated on the handle. A coil spring interposed between the handle and the movable member urges the two sleeves to be maintained at distance one from each other. The blade of the instrument to be bent is engaged between the two sleeves when they are positioned distant from each other. A force then is exerted on the movable member for moving one of the sleeves toward the other one and pinching the blade of the instrument between them. Then, while the blade is pinched between the sleeves, a traction is exerted on the instrument accompanied with a lateral displacement that produces the bending of the blade.

7 Claims, 1 Drawing Sheet

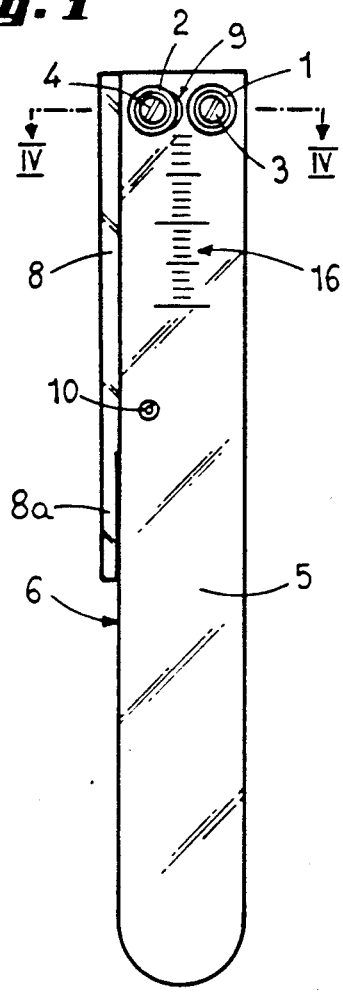
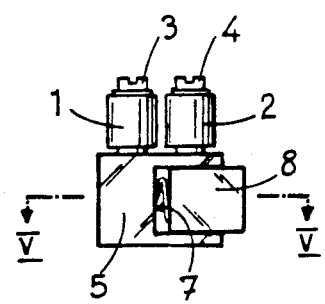
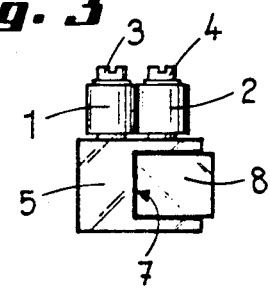
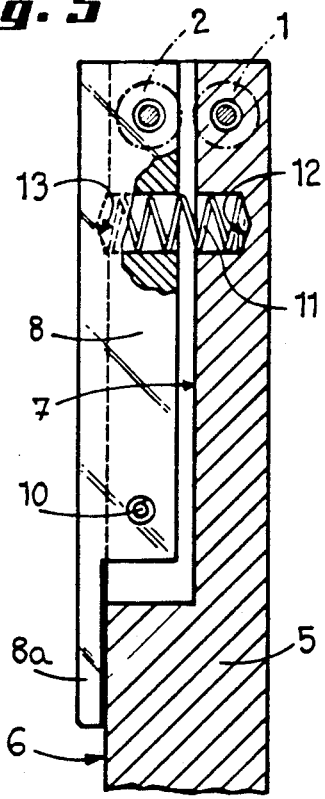
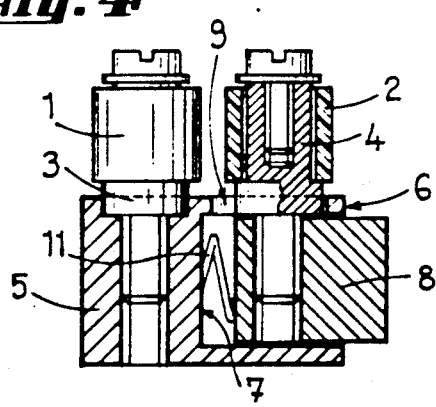

APPARATUS FOR BENDING DENTAL ROOT CANAL INSTRUMENTS

BACKGROUND OF THE INVENTION (a) Field of the Invention

The present invention is concerned with an apparatus for bending or curving dental instruments for use in root canals.

(b) Description of the Prior Art

The dental instruments used in root canals such as files, reamers or the like, the diameter of which is of some tenths of a millimeter, are sold to the dentists in their rectilinear state. They are suitable, in this condition, for the treatment of rectilinear root canals.

When it is matter of treating curved root canals, which is frequently the case, the introduction into such canals of the rectilinear instrument can give rise to some difficulties in spite of the flexibility of the instrument resulting from the fineness of its stem. It is for this reason that dentits attempt to pre-bend or pre-curve the instrument, by means of tweezers which are not suitable tools for such purpose and which in most cases results in the production, on the stem of the instrument, of an elbow rather than a curved portion. Rather than facilitating the use of the instrument, this has the contrary effect.

SUMMARY OF THE INVENTION

The object of the present invention is to provide a solution to the problem of bending or curving the dental instruments for use in root canals.

To this end, the apparatus according to the invention comprises two juxtaposed stems movable with respect to each other, means the stems to approach each other against the action of a resilient return device urging the stems to separate them one from another, the arrangement being such that, while engaging an instrument to be bent between said stems and while moving the stems one to each other until pinching the said instrument user can by, withdrawing the instrument while imparting thereto a lateral displacement, impart to the instrument a curved shape corresponding to the shape of the root canal to be treated.

The various features of the invention will be apparent from the following description, drawings and claims, the scope of the invention not being limited to the drawings themselves as the drawings are only for the purpose of illustrating ways in which the principles of the invention can be applied. Other embodiments of the invention utilizing the same or equivalent principles may be used and structural changes may be made as desired by those skilled in the art without departing from the present invention and the purview of the appended claims.

BRIEF DESCRIPTION OF THE DRAWINGS

FIG. 1 is an elevational view of an apparatus for bending or curving dental instruments for use in root canals.

FIG. 2 is an end view thereof.

FIG. 3 is also an end view of the apparatus, represented in a position which is different from that of FIG. 2.

FIG. 4 is a sectional view taken along the line IV—IV of FIG. 1.

FIG. 5 is an enlarged sectional view taken along the line V—V of FIG. 2, and

FIG. 6 is an elevational view of a file for treating root canals bent by means of the apparatus of FIGS. 1 to 5.

DESCRIPTION OF THE PREFERRED EMBODIMENTS

The apparatus illustrated comprises two cylindrical sleeves 1 and 2 made of plastic material rotatably mounted on two journals 3 and 4, respectively. The journal 3 is screwed on a stationary supporting element 5 of elongated shape, substantially parallelepipedic, to act as a handle. The stationary supporting element 5 is provided, opening on one of its lateral faces, designated by 6, with a recess 7 of rectangular section.

The journal 4 is screwed on a movable supporting member 8 of elongated shape, of rectangular section, engaged in the recess 7 of the stationary supporting element 5; the journal 4 traverses an elongated opening 9 (FIGS. 1 and 4) provided in the element 5. The movable member 8 is articulated on the element 5 by means of a stud 10. A coil spring 11 is engaged by one of its ends in a hole 12 provided in the bottom of the recess 7 of the stationary supporting element 5 and by its other end in a hole 13 provided in the movable member 8.

Spring 11 urges the member 8 to be maintained in its position in which the sleeves 1 and 2 are separated from each other (FIGS. 1, 2, 4 and 5). In the separated position, an extension 8a of the member 8 which extends beyond the articulation stud 10 along the lateral face 6 of the element 5 bears on the element 5.

The apparatus as disclosed and represented is used as follows:

The instrument for use in root canals could be, for instance, a file such as that which is represented in FIG. 6, comprising a handle 14 into which is driven a stem 15 constituting the blade of the apparatus which is provided with a smooth portion at its root and an active cutting portion at its end. The bending of the instrument is achieved while gripping with one hand, for instance with the left hand, the element 5 which acts as a handle, the thumb being applied on the movable member 8. While the apparatus is held this way, the dentist engages the blade 15 of the instrument it holds with the other hand between the sleeves 1 and this step is easy to be accomplished since these sleeves are then separated from each other. The dentist the exerts with the thumb of the left hand a pressure on the movable member 8 of his apparatus, which movable member acts as a lever of the third type, until the blade 15 of the instrument is pinched between the two sleeves 1 and 2. The dentist withdraws the instrument, not longitudinally because to do so would not have any bending effect, but laterally, curve or bend the end of the blade 15, as shown in FIG. 6. The instrument which has been in this manner can easily be engaged into a curved dental root canal.

So as to permit to the dentist curve only a portion of the length of the blade of the instrument, measured from the point of the instrument, the element 5 carries a graduation, indicated at 16 in FIG. 1, which permits to measurement of the length of the blade of the instrument situated beyond the point of contact between the blade and the sleeves 1 and 2.

What is claimed is:

1. Apparatus for bending dental instruments for use in root canals comprising, a stationary elongated supporting element, an elongated member pivotally mounted on said elongated supporting element about a pivot axis, resilient return means urging said elongated supporting element and elongated member to be separated from each other about said pivot axis, a first stem having an axis and mounted at one end of the elongated supporting element, a second stem having an axis and mounted at one end of the elongated member, the stems being juxtaposed and mounted with their respective axis oriented parallel to each other, said pivot axis being parallel to the axis of said stems, the stems being movable toward each other when the elongated member is pivoted toward said elongated supporting element, whereby a dental instrument may be pinched between said stems and withdrawn therefrom to impart a curved shape to said instrument.

2. Apparatus as claimed in claim 1, in which the two stems are formed as generally cylindrical sleeves each rotatably mounted on a stationary journal.

3. Apparatus as claimed in claim 2, in which said sleeves are constructed of plastic material.

4. Apparatus as claimed in claim 1 in which the elongated supporting element includes a handle portion, the handle portion having a recess and the elongated member being engaged within the recess, whereby movement of the elongated member in the recess moves said second stem toward said first stem.

5. Apparatus as claimed in claim 4 in which said resilient means is a coil spring interposed between the elongated supporting element and the elongated member to urge the same apart to separate said stems from each other, said elongated member including abutment means to bear against the elongated supporting element when the element and member are urged apart.

6. Apparatus as claimed in claim 5 in which said abutment means include an extension formed on said elongated member positioned against the handle portion outside of said recess.

7. Apparatus as claimed in claim 4 in which said elongated supporting element includes a graduation scale etched on one surface thereof to indicate the length of the instrument positioned between the stems.

* * * * *